(12) United States Patent
Laubert

(10) Patent No.: US 10,603,187 B2
(45) Date of Patent: Mar. 31, 2020

(54) SPINAL INTERBODY DEVICE, SYSTEM AND METHOD

(71) Applicant: AESCULAP IMPLANT SYSTEMS, LLC, Center Valley, PA (US)

(72) Inventor: Nikolay Laubert, Center Valley, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 1310 days.

(21) Appl. No.: 13/944,545

(22) Filed: Jul. 17, 2013

(65) Prior Publication Data

US 2015/0025635 A1 Jan. 22, 2015

(51) Int. Cl.
*A61F 2/44* (2006.01)
*A61F 2/30* (2006.01)
(Continued)

(52) U.S. Cl.
CPC .......... *A61F 2/447* (2013.01); *A61F 2/30942* (2013.01); *A61F 2/30965* (2013.01); *A61F 2/4611* (2013.01); *A61B 17/7059* (2013.01); *A61F 2002/2835* (2013.01); *A61F 2002/305* (2013.01); *A61F 2002/30431* (2013.01); *A61F 2002/30451* (2013.01); *A61F 2002/30578* (2013.01); *A61F 2002/30593* (2013.01); *A61F 2002/30604* (2013.01); *A61F 2002/30777* (2013.01); *A61F 2002/30787* (2013.01); *A61F 2002/30789* (2013.01); *A61F 2002/30828* (2013.01); *A61F 2002/4629* (2013.01); *A61F 2310/00017* (2013.01); *A61F 2310/00023* (2013.01); *A61F 2310/00047* (2013.01); *A61F 2310/00161* (2013.01);
(Continued)

(58) Field of Classification Search
CPC ............ A61F 2/447; A61F 2002/30504; A61F 2002/30604; A61F 2002/448
See application file for complete search history.

(56) References Cited

U.S. PATENT DOCUMENTS 3,577,608 A * 5/1971 Texler .................. A44B 99/005
24/594.11
3,986,780 A * 10/1976 Nivet ...................... F16B 21/02
403/353

(Continued)

FOREIGN PATENT DOCUMENTS

| EP | 2 018 827 A1 | 1/2009 |
|---|---|---|
| WO | 2007/065993 A2 | 6/2007 |
| WO | 2012/056119 A1 | 5/2012 |

OTHER PUBLICATIONS

The extended European search report for the related European Patent Application No. 15181356.5 dated Feb. 2, 2016.

*Primary Examiner* — Jacqueline T Johanas
(74) *Attorney, Agent, or Firm* — Kenealy Vaidya LLP

(57) ABSTRACT

A spinal interbody device, system and method can include use of an interbody cage and plate. The interbody cage can include at least one of a key and a keyway configured to mate with at least one of a mating keyway and key located on the plate. The key and keyway can be configured such that the cage and plate are quickly and easily attached and detached from each other, and such that positional relationship between the cage and plate can be arrived at quickly, accurately, and with tactile and/or audile notice to the practitioner.

23 Claims, 14 Drawing Sheets

(51) Int. Cl.
   *A61F 2/46* (2006.01)
   *A61B 17/70* (2006.01)
   *A61F 2/28* (2006.01)

(52) U.S. Cl.
   CPC ............... *A61F 2310/00179* (2013.01); *A61F 2310/00359* (2013.01); *Y10T 29/49826* (2015.01)

(56) References Cited

U.S. PATENT DOCUMENTS

| | | | |
|---|---|---|---|
| 4,467,987 A * | 8/1984 | Small | F16B 21/02 248/68.1 |
| 4,893,978 A * | 1/1990 | Frano | A44B 99/005 24/297 |
| 5,257,993 A * | 11/1993 | Asher | A61B 17/7032 606/300 |
| 5,382,251 A * | 1/1995 | Hood | A61B 17/320068 606/99 |
| 5,531,554 A | 7/1996 | Jean-Francois et al. | |
| 5,683,394 A * | 11/1997 | Rinner | A61F 2/4455 606/247 |
| 6,235,059 B1 | 5/2001 | Benezech et al. | |
| 6,849,093 B2 * | 2/2005 | Michelson | A61F 2/446 623/17.11 |
| 7,112,222 B2 | 9/2006 | Fraser et al. | |
| 7,172,627 B2 | 2/2007 | Fiere et al. | |
| 7,850,731 B2 | 12/2010 | Brittan et al. | |
| 8,034,086 B2 * | 10/2011 | Iott | A61B 17/7032 606/267 |
| 8,216,312 B2 * | 7/2012 | Gray | A61B 17/7059 606/249 |
| 8,377,132 B2 | 2/2013 | Wing et al. | |
| 8,998,956 B2 * | 4/2015 | George | A61B 17/0642 606/250 |
| 9,005,293 B2 | 4/2015 | Moskowitz et al. | |
| 9,987,143 B2 * | 6/2018 | Robinson | A61F 2/447 |
| 2001/0020185 A1 * | 9/2001 | Ray | A61F 2/446 623/17.11 |
| 2002/0147450 A1 * | 10/2002 | LeHuec | A61B 17/1671 606/86 B |
| 2004/0225362 A1 * | 11/2004 | Richelsoph | A61F 2/4425 623/17.13 |
| 2006/0276793 A1 | 12/2006 | Berry | |
| 2008/0221695 A1 * | 9/2008 | Jacofsky | A61F 2/447 623/17.16 |
| 2008/0294262 A1 | 11/2008 | Levieux | |
| 2010/0272540 A1 * | 10/2010 | Bucker | F16B 21/02 411/549 |
| 2010/0292794 A1 * | 11/2010 | Metz-Stavenhagen | A61F 2/44 623/17.11 |
| 2010/0312345 A1 | 12/2010 | Duffield et al. | |
| 2011/0160866 A1 * | 6/2011 | Laurence | A61B 17/1671 623/17.16 |
| 2011/0190892 A1 * | 8/2011 | Kirschman | A61F 2/44 623/17.16 |
| 2011/0251689 A1 * | 10/2011 | Seifert | A61F 2/442 623/17.16 |
| 2011/0253579 A1 * | 10/2011 | Chong | B65D 73/0014 206/493 |
| 2011/0288590 A1 * | 11/2011 | O'Farrell | A61B 17/7059 606/264 |
| 2012/0078373 A1 | 3/2012 | Gamache et al. | |
| 2012/0277868 A1 * | 11/2012 | Walters | A61F 2/442 623/17.16 |
| 2012/0277873 A1 * | 11/2012 | Kana | A61F 2/447 623/17.16 |
| 2013/0018470 A1 | 1/2013 | Moskowitz et al. | |
| 2013/0073044 A1 | 3/2013 | Gamache | |
| 2013/0158667 A1 * | 6/2013 | Tabor | A61F 2/4455 623/17.16 |
| 2013/0218726 A1 * | 8/2013 | Steiner | G06Q 30/06 705/26.81 |
| 2013/0268076 A1 * | 10/2013 | Carlson | A61F 2/446 623/17.16 |
| 2014/0039623 A1 * | 2/2014 | Iott | A61F 2/30744 623/17.16 |
| 2014/0259565 A1 * | 9/2014 | Hirama | F16L 3/223 24/455 |
| 2014/0358244 A1 * | 12/2014 | Hakansson | A61F 2/4261 623/21.12 |
| 2016/0367379 A1 * | 12/2016 | Refai | A61F 2/447 |
| 2018/0243104 A1 * | 8/2018 | Garonzik | A61F 2/447 |

\* cited by examiner

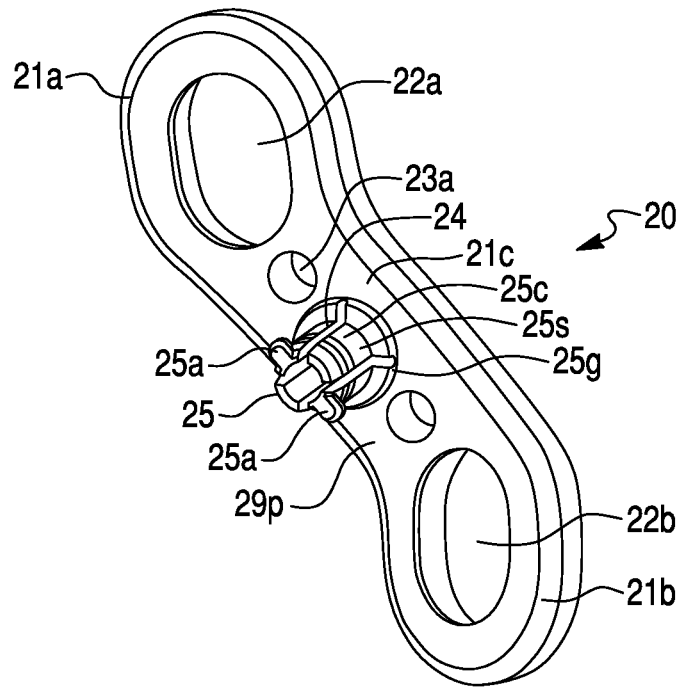
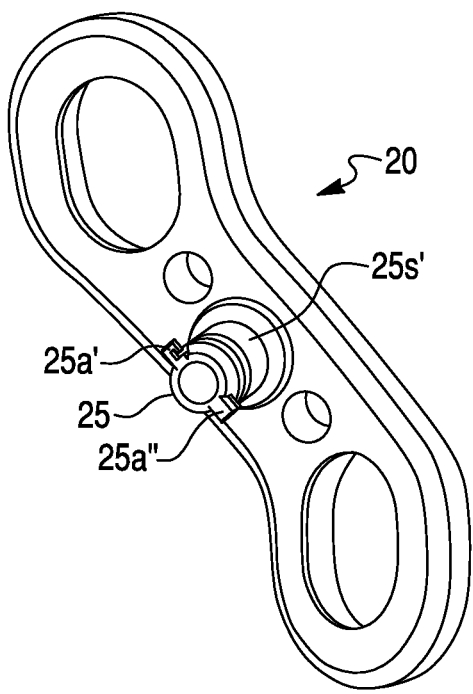
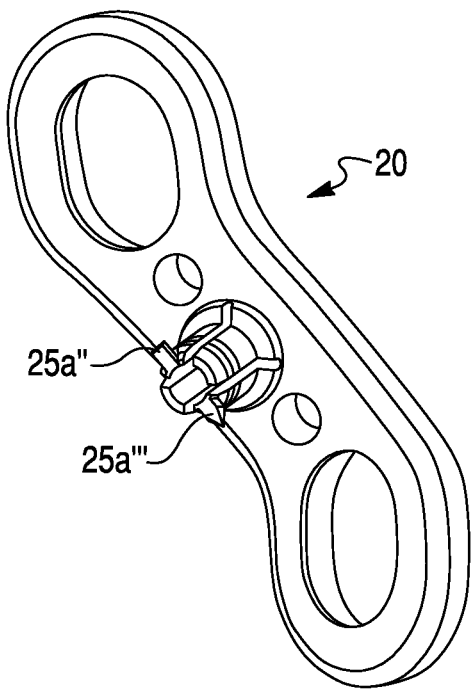

SPINAL INTERBODY DEVICE, SYSTEM AND METHOD

BACKGROUND

1. Field

The presently disclosed subject matter relates generally to surgical instrumentation devices, systems, and related methods, and more specifically to a spinal interbody device, system and method for use in implanting an interbody device between adjacent or separate (i.e. neighboring but not necessarily naturally adjacent) vertebrae.

2. Description of the Related Art

In order to stabilize two adjacent or separate vertebrae of the spine, medical professionals will typically place a first component, commonly referred to as a cage, between adjacent target vertebrae. The cage will then be secured to the vertebrae using bone screws that traverse angled apertures in the cage to attach to upper and lower target vertebrae. Sometimes, a second component, typically referred to as a plate, is attached to both the cage and the upper and lower target vertebrae. The plate acts to further secure the cage in position and prevents back-out and/or movement or migration of the cage itself. The plate is configured to bridge the adjacent vertebrae and attach to the vertebrae via bone screws or similar structure. The placement of the first and second components is often performed in a serial fashion which can increase the time required for surgery. Additionally, different insertion instruments have been used for each of the plate and the cage components.

More specifically, anterior interbody fusion is a common technique for treating injured, diseased, or otherwise damaged vertebrae and/or disc(s) from an anterior approach. The anterior approach allows access to an interbody space with minimal damage to the posterior musculature, while allowing full decompression and/or stabilization of the diseased or damaged disc or vertebrae. The cage can include an interbody hollow or open area configured to receive bone graft or other bonding, grafting or regenerative material(s). The regenerative or bonding materials promote fusion of the adjacent vertebrae together.

Recently, there have been efforts to integrate the plate and cage components into either a unified or mechanically coupled device. Such a unified device creates efficiency for the practitioner by reducing the number of implantation steps and instruments.

SUMMARY

Accordingly, it may be beneficial to provide a combination cage-plate device in which the attachment structures can be operated with speed and accuracy while also providing consistent locking between the cage and plate components at a precise and relative position. In addition, a need has been uncovered for a device that has a low profile while providing the above-referenced features. In addition to the above, a need has been uncovered for a stand alone interbody device intended for use in the cervical region (C3 through C7) of the spine that provides the features of, for example, restoration of disc height, an ability to be fixed to vertebral bodies, and an ability to create opportunities for spinal fusion in cases of degenerative instability, post-discectomy syndrome and post-traumatic instability in the C3-C7 region.

According to one aspect of the disclosure, a spinal interbody device can include a cage configured to be inserted between adjacent vertebrae of a spinal column, and a plate. The cage can include at least one aperture and at least one of a key and a keyway. The plate can include at least one of a mating key and a mating keyway, and can be configured to be attached to the cage at an exterior surface of the cage. The plate can include at least one aperture configured to accommodate an attachment structure when the interbody device is in use. One of the key and the mating key can include a shaft extending from a respective one of an anterior surface of the cage and a posterior surface of the plate. The one of the key and the mating key can further include at least one flange extending from a distal end of the shaft. The shaft can be cylindrical and slotless, or can include a slot extending in a direction parallel with a longitudinal axis of the shaft such that the shaft is divided into at least two spring portions. The at least one flange can be located at a distal end of one of the at least two spring portions such that the at least one flange is moveable towards and away from the longitudinal axis of the shaft under bias of the one of the at least two spring portions. The two flanges can each be formed as substantially flat planar extensions substantially perpendicular to a longitudinal axis of the shaft. The at least one of the key and mating key, and the at least one of the keyway and mating keyway, can be configured such that the plate and cage are freely moveable towards each other when the at least one of the key and mating key is located in the at least one of the keyway and mating keyway, and such that the plate and cage lock with respect to each other when rotated a predetermined amount with respect to each other. The plate can be configured as an "S-shaped" structure having a center portion with a longitudinal axis extending between a top end and a bottom end of the center portion. The plate can also include a top extension with a top longitudinal axis extending from the top end of the center portion and at an angle away from the longitudinal axis of the center portion, and a bottom extension with a bottom longitudinal axis extending from the bottom end of the center portion and at an angle away from the longitudinal axis of the center portion.

According to another aspect of the disclosed subject matter, a spinal interbody system can include a cage configured to be inserted between adjacent vertebrae of a spinal column. The cage can include a keyway extending from an exterior surface of the cage to an interior surface in the cage. The system can also include a plate having a key configured to be attached via the keyway to the cage such the plate can be moved between an unlocked position and a locked position relative to the cage. The key and keyway can be configured such that the plate is prevented from rotational movement relative to the cage during a first linear movement portion of the plate towards the cage, and such that the plate is prevented from linear movement relative to the cage during a second rotational movement portion of the plate relative to the cage.

According to another aspect of the disclosed subject matter, a method for use of a spinal interbody device can include providing a spinal cage including at least one of a key and a keyway, and a plate including at least one of a mating key and a mating keyway. The method can further include placing the spinal cage between adjacent vertebrae in a spinal column, and inserting one of the key and the mating key into a respective one of the of the keyway and mating keyway by moving at least one of the spinal cage and the plate closer to each other along a substantially linear path and with no relative rotation between the cage and plate while moving along the substantially linear path. The method can also include rotating at least one of the spinal cage and the plate with respect to each other such that rotating causes the spinal cage and the plate to be locked together. Once locked together, the user or practitioner can be confident that correct alignment and installation of the device can be achieved during use.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which:

FIG. 2A is a perspective posterior view of the plate of FIG. 1.

FIG. 2B is a perspective posterior view of another embodiment of a plate made in accordance with principles of the disclosed subject matter.

FIG. 2C is a perspective posterior view of another embodiment of a plate made in accordance with principles of the disclosed subject matter.

DETAILED DESCRIPTION OF EXEMPLARY EMBODIMENTS

Figure 1:
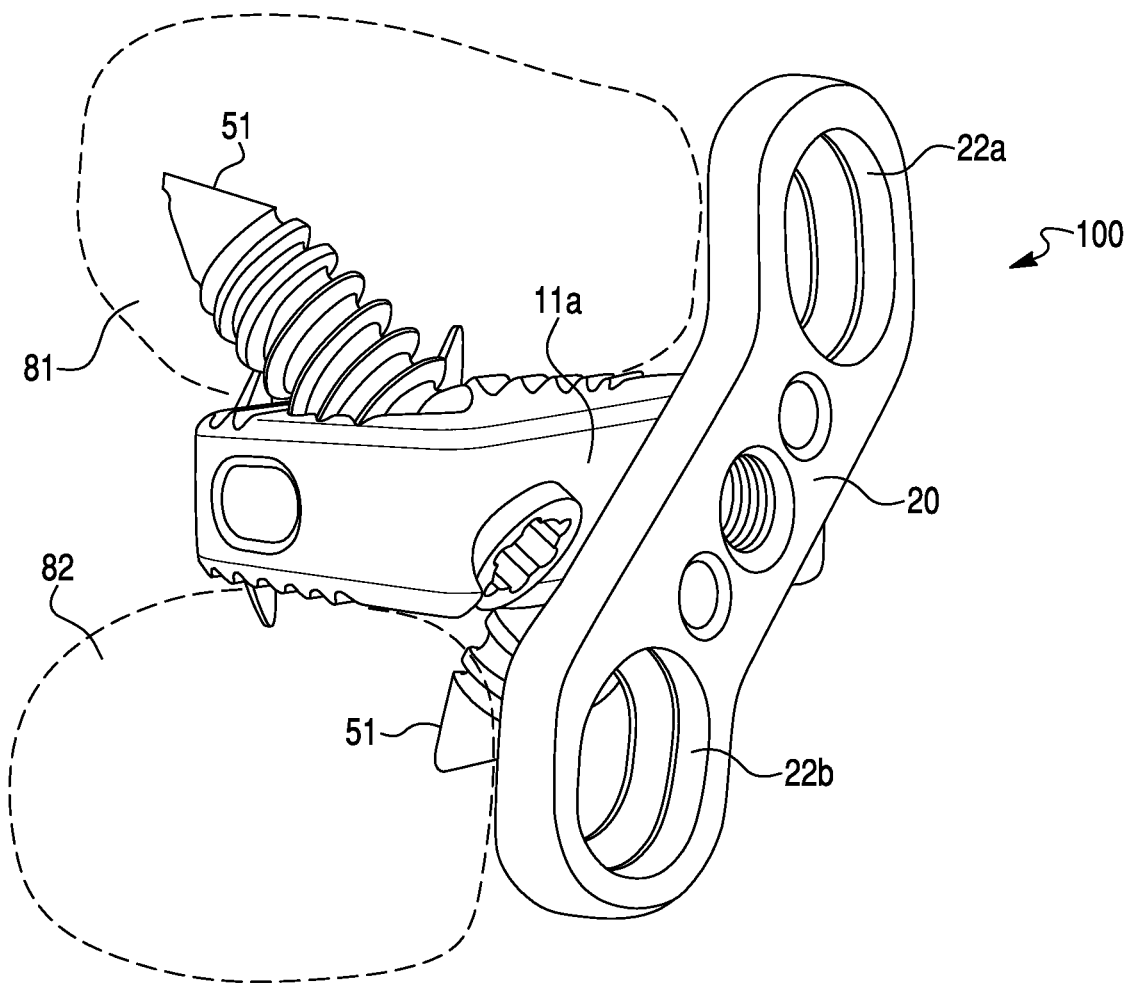
FIG. 1 is a perspective anterior view of a cage and plate device and system made in accordance with principles of the disclosed subject matter.

FIG. 1 is a perspective anterior view of one exemplary embodiment of an interbody device/system 100 made in accordance with principles of the disclosed subject matter. The interbody device/system 100 can include a cage 10 and a plate 20 that can be locked into position with respect to each other and molded, machined, printed, or otherwise formed as separate structures. The cage 10 can be configured as a generally cuboid structure suitable for placement between adjacent vertebrae 81, 82. In one embodiment, the cage 10 is intended to be used in the cervical region (C3 through C7) of the spine. The cage 10 can also be shaped so as to provide restoration of disc height when placed between the vertebrae 81, 82 and to generally mimic the spacing and structure of an intervertebral disk in this region. A plate 20 can be provided for attachment to an anterior surface 11a of the cage 10. In the locked position, as shown in FIG. 1, the plate 20 includes an upper aperture 22a and a lower aperture 22b, each configured to house a bone attachment structure for connecting the plate 20 to each of the vertebrae 81, 82. Thus, the interbody device/system 100 can include four separate attachment structures for attachment to the vertebrae 81, 82 at four separate locations, e.g., to the inferior surface and anterior surface of vertebra 81 and to the superior surface and anterior surface of vertebra 82. The cage 10 and plate 20 can be configured for use in many different medical and surgical procedures, including to create opportunities for spinal fusion in cases of degenerative instability, post-discectomy syndrome, post-traumatic instability, and other diseases, injuries, or malformations in the spine, and particularly in the C3-C7 region.

FIG. 2A is a perspective posterior view of the plate 20 which, in one embodiment, can be configured as an "S-shaped" structure having a center portion 21c located between an upper or top extension portion 21a and a lower or bottom extension portion 21b. The central portion 21c can include a longitudinal axis extending between the top extension portion 21a and the bottom extension portion 21b. Each of the extension portions 21a, 21b can also include a respective longitudinal axis that extends at an angle (an angle greater than zero degrees and less than 180 degrees) away from the longitudinal axis of the center portion. An upper aperture 22a can be provided in the top extension portion 21a, and a lower aperture 22b can be provided in the bottom extension portion 21b. The apertures 22a, 22b can be configured to allow a bone attachment structure to pass through in order to secure the plate 20 to anterior surfaces of adjacent vertebrae. Thus, the apertures 22a, 22b can be configured as circular apertures, ovoid apertures, slots, polygonal apertures, non-symmetrical apertures or the like depending on the shape and type of bone attachment structure to be used with the plate 20. For example, a typical bone screw having a rounded or tapered head could be used with the plate 20. However, different types of attachment heads could be used and different types of attachment structures could be used, such as pins, barbs, rivets, trocars, cements, and other adhesive or attachment structure.

A key 25 can be located at the center portion 21c of the plate 20. The key 25 can be integrally formed with the posterior surface 29p of the plate 20 such that the entire plate 20 is constructed from a continuous (same) material. Alternatively, the key 25 can be separately formed and attached to the posterior surface 29p of the plate 20 by an attachment structure or mechanism, such as screw threading, clip, separate attachment structures, welding, or other attachment structure or mechanism. In this embodiment, the key 25 is integrally formed and extends from a central axis of the plate 20. A boss 25g is formed at the base of the key 25 where the key 25 extends from the posterior surface 29p of the plate 20. The key 25 can include a shaft 25s with a longitudinal axis extending substantially (i.e., totally or almost totally) perpendicular with respect to the posterior surface 29p of the plate 20.

The shaft 25s of the key 25 can include a plurality of slots 24 that extend parallel with the longitudinal axis of the shaft 25s such that the shaft is divided into a plurality of key sub-sections 25c. Thus, each of the key subsections 25c can be moved relative to each other under relative bias. When moved, the key subsections 25c will be biased back towards a neutral position.

At least one flange 25a can be located at a distal end of the shaft 25s. The flange 25a is shown as being shaped as a substantially semi-circular lobe. However, the flange 25a can take on many different shapes that can perform the appropriate keyway function depending on application, design choice, or other criteria. For example, the flange 25a can be rectangular, square, triangular, or other polygonal shape. In addition, the flange 25a can be curved in a semi-oval shape, non-symmetrical shape, symmetrical curved free form shape, or other shape. If more than one flange 25a is located at the distal end of shaft 25s, each of the flanges 25a can have the same or different shapes. If the flanges 25a are differently shaped, the user may be required to orient the plate 20 with respect to the cage in only one relative attachment position, thus assisting in consistent and repeatable quick attachment between the two structures when specific orientation is desired. Further, the flange 25a can be a three dimensional structure such as a hemisphere or other dimple or button shaped structure. Additionally, the flange 25a can be oriented and configured to include opposing flat surfaces that are either substantially perpendicular to a longitudinal axis of the key, or substantially parallel with the longitudinal axis of the key, or other orientation.

FIG. 2B shows a specific exemplary embodiment of a plate 20 in which the key 25 includes a first flange 25a' that is formed in a non-symmetrical shape and is different from a second directly opposing flange 25a" which is formed in a substantially rectangular shape. The shaft 25s' of the key 25 is a solid shaft with no slits running parallel with the longitudinal or central axis of the key 25.

FIG. 2C shows yet another specific exemplary embodiment of a plate 20 in which the key 25 includes a first flange 25a" which is formed in a substantially rectangular shape. The shaft 25s of the key 25 can be a solid shaft with no slits running parallel with the longitudinal or central axis of the key 25. A second flange 25a''' can be formed as a pyramidal shape that is polygonal (triangular) as viewed from above (along the longitudinal or central axis of the key 25) and extends a substantial distance above and below the otherwise flat top surface of the key 25 and lower flat surface of flange 25a". Thus, the flange 25a''' provides an example of a flange that has three-dimensional characteristics.

Figure 3A:
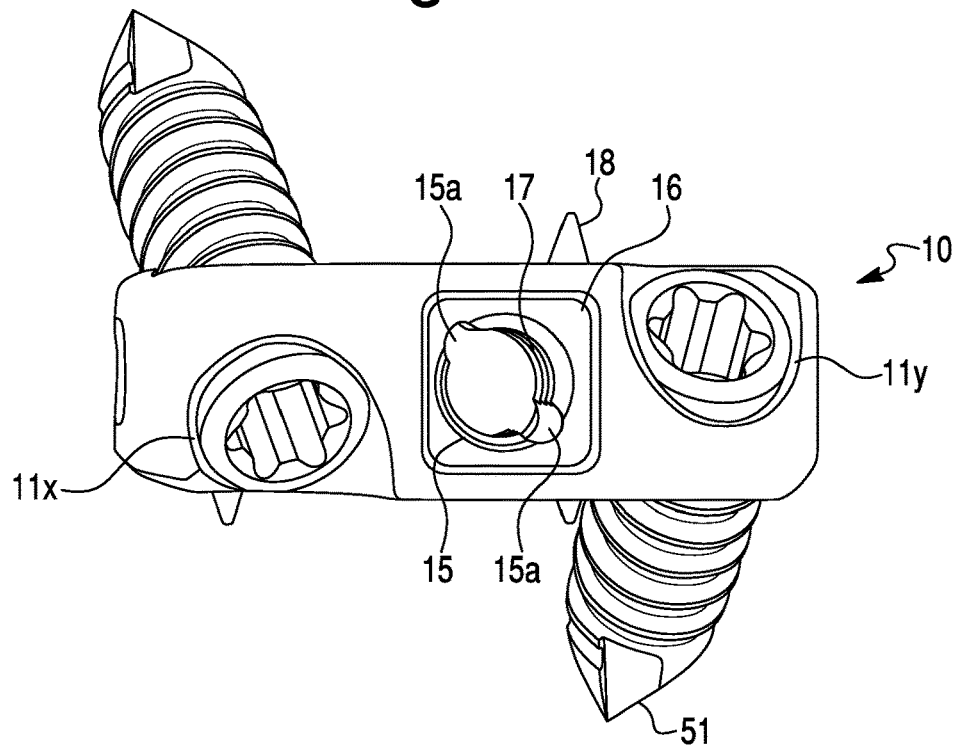
FIG. 3A is a front view of the anterior surface of the cage of FIG. 1.

FIG. 3A is a front view of the anterior surface of the cage 10. In this view, an exemplary keyway 15 is shown as including a substantially (i.e., totally or almost totally) circular cylindrical aperture extending from the exterior anterior surface of the cage 10 to an interior portion of the cage 10. The keyway 15 can be located in a recess, such as square recess 16, located in the anterior face 11a of the cage 10. The recess can be configured to mate with a locking structure of the insertion tool 71 and can also be configured to mate with a structure, such as boss 25g, in the plate 20 to positively position the plate 20 relative to the cage 10 when they are joined together.

The keyway 15 can include at least one flange opening 15a extending from a periphery of the cylindrical aperture. The flange opening 15a can run along an interior face of the keyway 15 and parallel with the longitudinal axis of the cylindrical aperture. The cross-section shape of the flange opening 15a as viewed from a longitudinal/central/symmetrical axis of the keyway 15 (as viewed in FIG. 3A) can be shaped and dimensioned to match the shape and dimensions of one of the key flanges 25a. Thus, the keyway 15 and key flange opening 15a will allow the key 25 and key flanges 25a to pass therethrough. In addition, if keyway 15 and key flange opening 15a are constructed with appropriate tolerances with respect to the key flange 25a and key 25, the keyway 15 can provide some amount of support and guidance for the key 25 as it passes along the keyway 15.

Similar to the description above related to the many different shapes and orientations possible for constructing the flange portion 25a, the key flange opening(s) 15a can also be formed in many different shapes, sizes, dimensions and orientations. For example, the key flange opening(s) 15a can be rectangular, square, triangular, or other polygonal shape. In addition, the key flange opening(s) 15a can be curved in a semi-oval shape, non-symmetrical shape, symmetrical curved free form shape, or other shape. If more than one key flange opening 15a is located in the keyway 15, each of the key flange openings 15a can have the same or different general shape. If the key flange openings 15a are differently shaped, the user may be required to orient the plate 20 with respect to the cage 10 in only one relative position for attachment, thus assisting in consistent and repeatable quick attachment between the two structures when specific orientation is desired. Further, the key flange opening(s) 15a can be constructed such that it selectively allows different size or shape flange portions 25a to pass through, while not permitting other shaped flange portions 25a. In other words, various combinations of flange openings 15a and flange portions 25a can be designed to work together even though they do not perfectly match with respect to specific shape or size, etc. However, certain other combinations of flange openings 15a and flange portions 25a can be designed to not work together to ensure that certain plates 20 are never matched with certain cages 10.

Figure 3B:
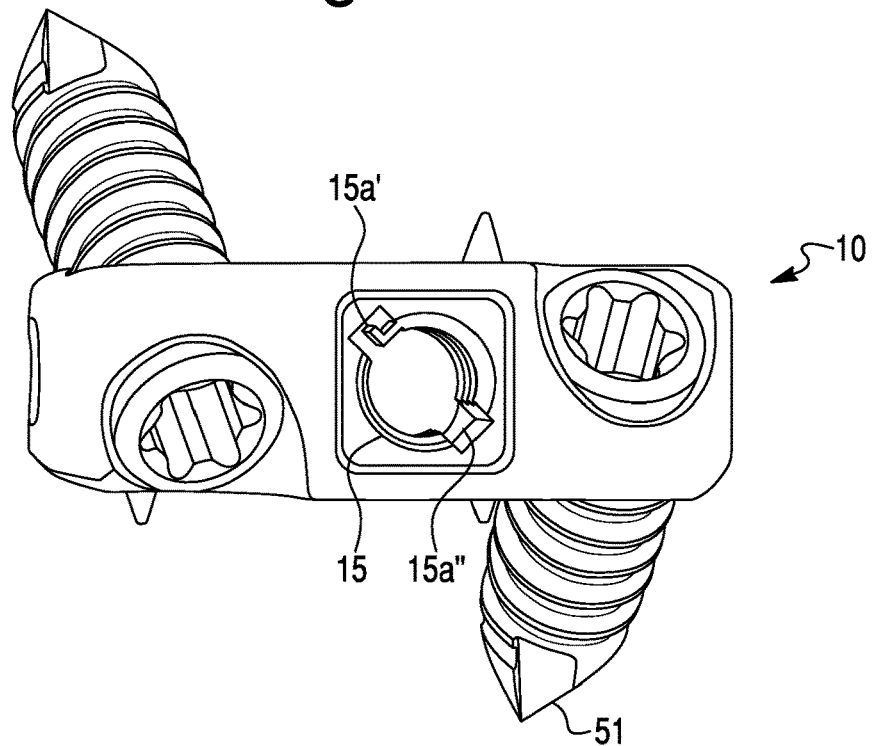
FIG. 3B is a front view of the anterior surface of another embodiment of a cage made in accordance with principles of the disclosed subject matter.

FIG. 3B is a front view of the anterior surface of another exemplary cage 10 in which keyway 15 includes a first non-symmetrical flange opening 15a' that is directly opposed to a substantially rectangular flange opening 15a". Thus, it would be possible for the plate shown in FIG. 2B to mate with the cage shown in FIG. 3B.

Figure 3C:
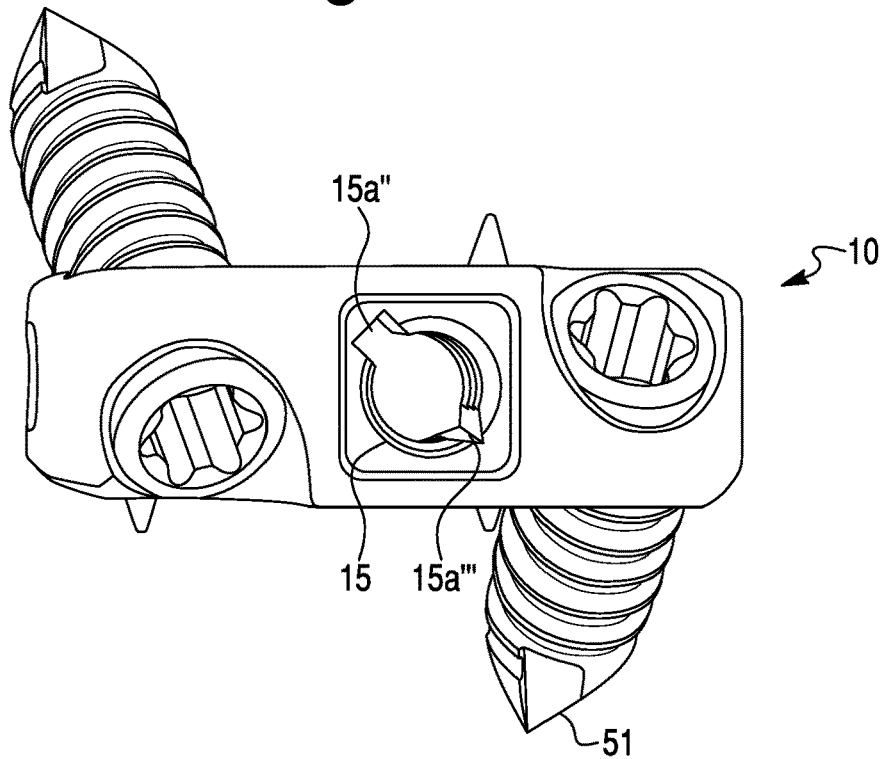
FIG. 3C is a front view of the anterior surface of another embodiment of a cage made in accordance with principles of the disclosed subject matter.

FIG. 3C is a front view of the anterior surface of another exemplary cage 10 in which keyway 15 includes a first substantially rectangular flange opening 15a". In addition, the keyway 15 includes a somewhat triangular flange opening 15a'''. The depth of the flange opening 15a''' can differ from the depth of the flange opening 15a" in order to accommodate a three dimensional flange therein. In addition, the depth of the flange opening 15a''' can be different from a depth of the flange opening 15a" in order to provide different locking characteristics when the plate 20 and cage 10 are rotated with respect to each other with the key 25 fit into the keyway 15. It may be possible for the plate shown in FIG. 2C to mate with the cage shown in FIG. 3C depending on the depth of the flange openings 15a" and 15a'''.

Figure 3D:
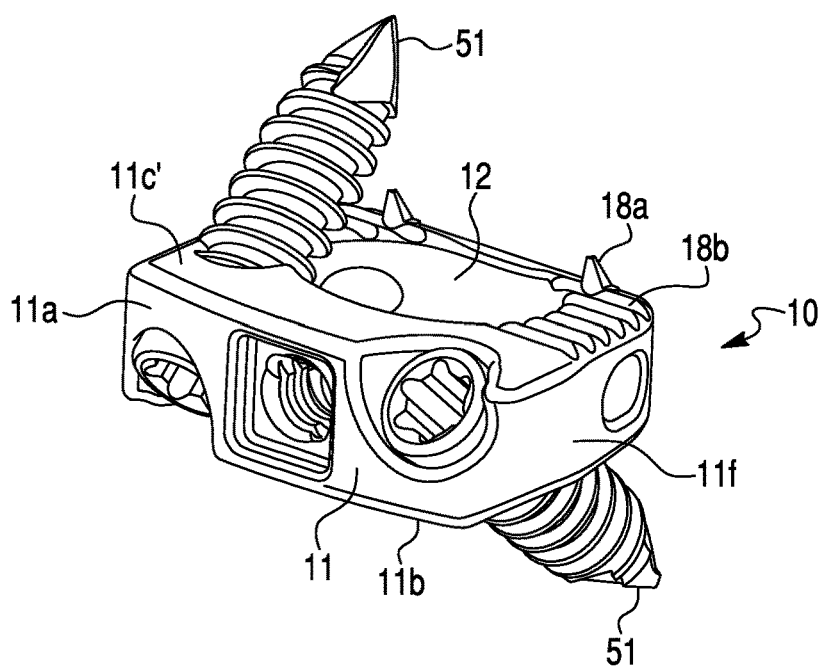
FIG. 3D is a perspective anterior view of the cage of FIG. 1.

FIG. 3D is a perspective anterior view of the cage 10 which can include a main cage aperture 12 designed to be filled with a bone regenerative material and/or biocompatible adhesive material that facilitates the fusing of the upper and lower vertebrae 81, 82, either immediately or over time, depending on surgical/medical treatment parameters and indications. The superior surface 11c' of the cage 10 can include the main cage aperture 12 that extends through to the inferior surface 11b of the cage 10. In addition, one or both of the superior surface 11c and inferior surface 11b can include locking projections, such as spikes 18a or grooves 18b. The locking projections 18a or 18b can be used to assist in both initial placement of the device and in long term prevention of migration of the cage 10 or plate 20 with respect to the vertebrae 81, 82. The cage 10 can also include medial and lateral openings that extend from the medial face 11e and lateral face 11f to the main cage aperture 12. These openings be designated for bone or other tissue in growth, can provide further anchor locations, or can be openings that simply reduce the overall weight of the device.

The locking projections, such as spikes 18a or grooves 18b, can be integral with the cage 10 or can be structure(s) that are separately attached to the cage 10. The locking projections 18a or 18b can also be located immediately adjacent the main cage aperture 12 such that the cage is prevented from movement relative to the adjacent vertebrae to which the cage 10 is attached. Thus, the cage 10 can promote stability between adjacent vertebrae and can also promote bone ingrowth into the cage 10 including the main aperture 12.

As shown in FIG. 3A, a left aperture 11x and a right aperture 11y can be provided in the anterior face 11a of the cage 10. The apertures 11x, 11y can extend from the anterior face 11a to the superior face 11c and inferior face 11b of the cage 10, respectively. The apertures 11x, 11y can also include a countersunk portion that allows a head of a screw 51 to fit neatly within each aperture 11x, 11y (i.e., with little or no portion of the screw 51 extending outside of a plane containing the anterior surface 11a). Thus, a screw 51 can be inserted through left aperture 11x and into vertebra 81 and another screw 51 can be inserted through right aperture 11y and into vertebra 82 to lock the cage 10 with respect to vertebrae 81, 82. Although the apertures 11x, 11y are shown as countersunk and generally circular cylindrical apertures, it is contemplated that the apertures 11x, 11y can be configured as ovoid apertures, slots, polygonal apertures, non-symmetrical apertures or the like depending on the shape and type of bone attachment structure to be used with the cage 10. For example, a typical bone screw 51 having a rounded or tapered head could be used with the cage 10. However, different types of attachment heads could be used, and different types of attachment structures could be used, such as pins, barbs, rivets, trocars, cements, and other adhesive or attachment structures.

Figure 4A:
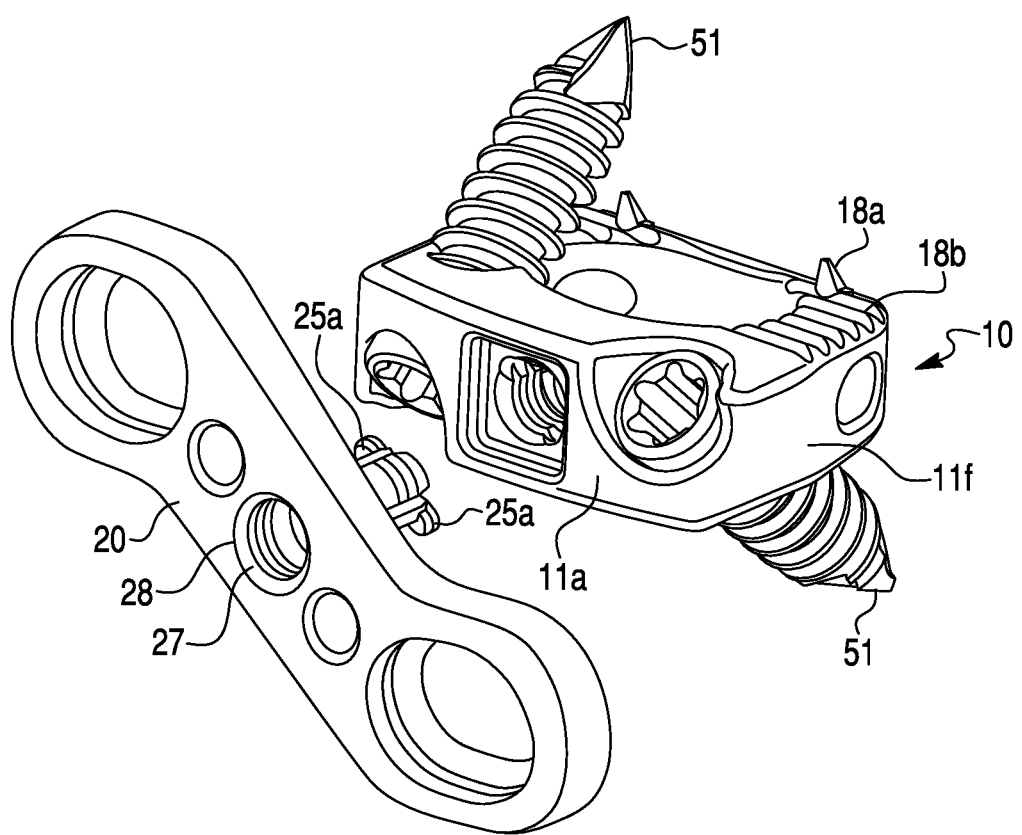
FIG. 4A is a perspective view of the cage and plate of FIG. 1 in a detached position.
Figure 4B:
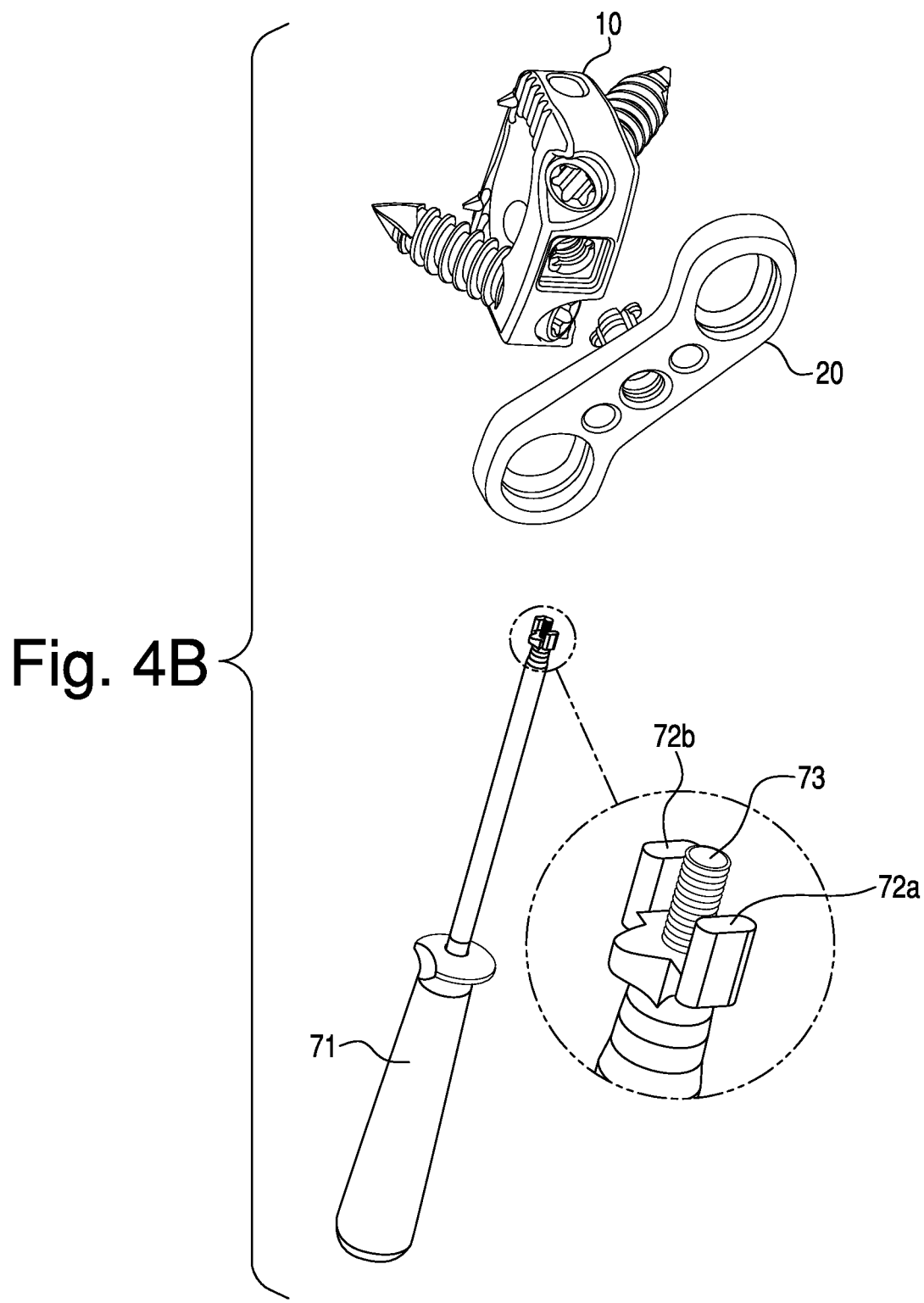
FIG. 4B is a perspective view of a system including the cage and plate of FIG. 1 and an insertion tool, made in accordance with principles of the disclosed subject matter.

FIG. 4A is a perspective view of the cage 10 and plate 20 in a detached position just prior to engagement and attachment. FIG. 4B shows an installation tool 71 that can be used in conjunction with placing one or both of the cage 10 and plate 20 in position relative to vertebrae 81, 82 (or relative to each other). The tool 71 can have a threaded end 73, and the plate 20 can include mating threads 27, such as M3 threads, located on an interior surface of a central opening that extends from an anterior surface of the plate 20 and through the key 25. Thus, the insertion tool 71 can lock onto the plate 20 via these mating threads. An installation upper aperture 23a and an installation lower aperture 23b can be provided in the plate 20 on respective sides of the key 25. Each of the apertures 23a, 23b can be configured to mate with prongs 72a, 72b of the insertion tool 71 during installation of the plate 20 onto the cage 10, or during installation of both the plate 20 and cage 10 into an intervertebral space. Thus, the plate 20 (or the plate 20 and cage 10) can be rotated together with the insertion tool 71.

The installation tool 71 (or a different installation tool) can also be used to attach solely to the cage 10 and facilitate placement of the cage 10 in an intervertebral space. In order to achieve attachment between the installation tool 71 and cage 10, the keyway can include threads 17, such as M3 threads, that mate with threads on the installation tool 71. A recess, such as square recess 16, can be provided in the anterior surface 11a of the cage 10 such that the recess mates with a similarly shaped portion of the insertion tool 71 when the insertion tool threads are locked onto the threads 17 of the cage. Thus, similar to the installation apertures 23a, b of the plate 20, the recess (square recess 16) will lock the tool 71 with the cage 10 such that no relative rotation can take place between the tool 71 and cage 10.

Figure 5A:
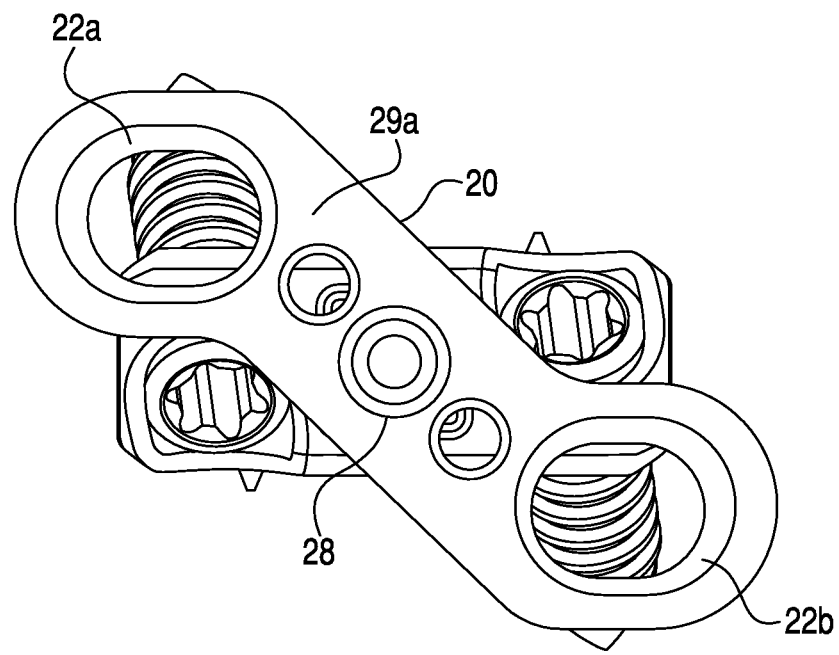
FIG. 5A is a front anterior view of the cage and plate of FIG. 1 in an initial attachment position.
Figure 5B:
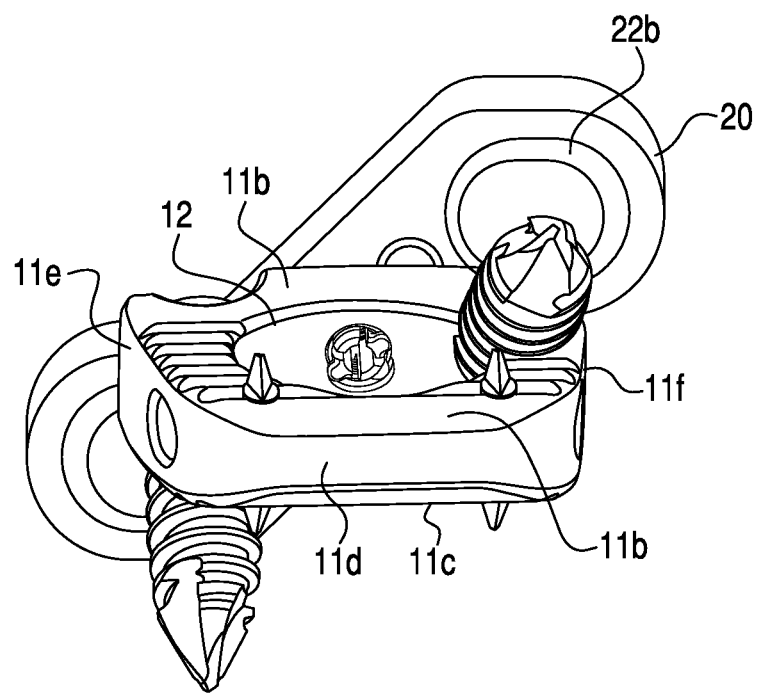
FIG. 5B is a rear posterior/inferior perspective view of the cage and plate of FIG. 5A in the initial attachment position.
Figure 5C:
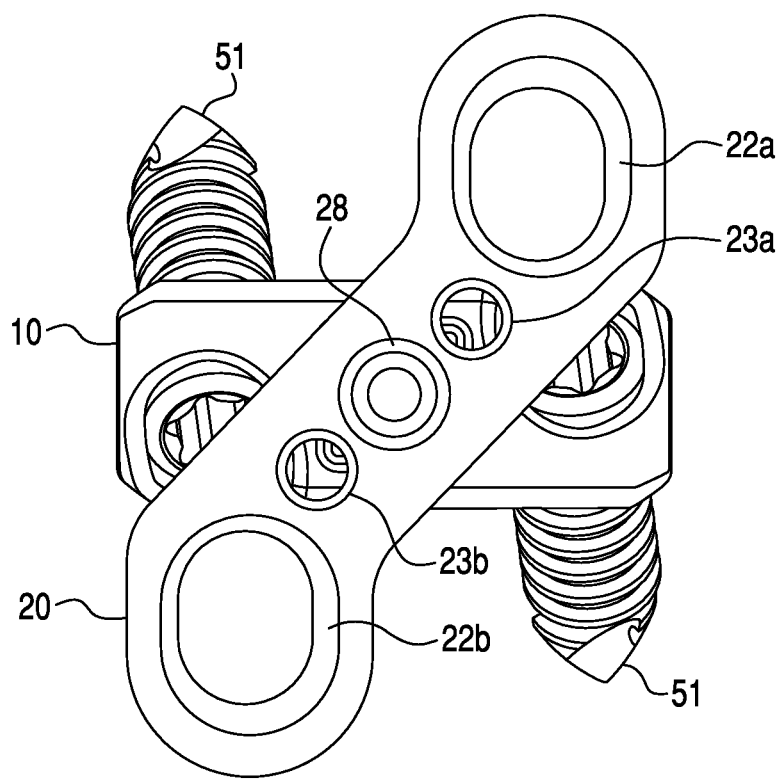
FIG. 5C is a front anterior view of the cage and plate of FIG. 1 in a final attachment position.

FIG. 5A-C depict sequential stages of an exemplary method for attaching the plate 20 to the cage 10. In FIG. 5A, the anterior surface 29a of a plate 20 is shown, with the plate 20 being oriented with respect to the cage 10 in such a way that the key 25 can freely slide along the central or longitudinal axis of the keyway 15. Thus, the cage 10 and plate 20 can move freely towards (or away from) each other in FIG. 5A, but are prevented from rotation with respect to each other while the key 25 is located in the keyway 15. Rotation can be prevented until the key 25 reaches a predetermined position within the keyway 15. FIG. 5B depicts the plate 20 and cage 10 when they are located at such a predetermined "motion transition" position. In this position, the key flanges 25a are located just outside of the keyway flange openings 15a and adjacent a lock rail 13. The key 25 (and plate 20) can now begin to rotate with respect to the keyway 15 (and cage 10) at this position, but are prevented from translating along or with respect to the longitudinal or central axis opening of the keyway 15. Specifically, the plate 20 can be rotated in a counterclockwise direction (as viewed in FIG. 5B) such that the key flanges 25a start to ride along and on top of the lock rail 13 located within keyway 15. The lock rail 13 prevents the key flanges 25a (and plate 20) from pulling back out of the keyway 15 after this rotation motion has begun. Likewise, the posterior surface of the plate 20 is in contact with the anterior surface of the cage 10 to limit further axial or translation movement between the cage 10 and plate 20 (i.e., to prevent further movement in the linear attachment direction between the cage 10 and plate 20).

Between FIGS. 5B and 5C, the plate 20 is rotated with respect to the cage 10 to a final locked position as shown in FIG. 5C. In this final locked position, the plate 20 can be configured such that a substantial portion of the attachment apertures 11x and 11y are covered by the plate 20. Thus, the screws 51 are prevented from backing out of the cage 10 (and prevented from backing out of the vertebrae 81, 82) when the plate 20 is located in the final locked position relative to the cage 10. The final locked position can be defined by a hard stop structure 19a located at a specific position along the lock rail 13.

Figure 6:
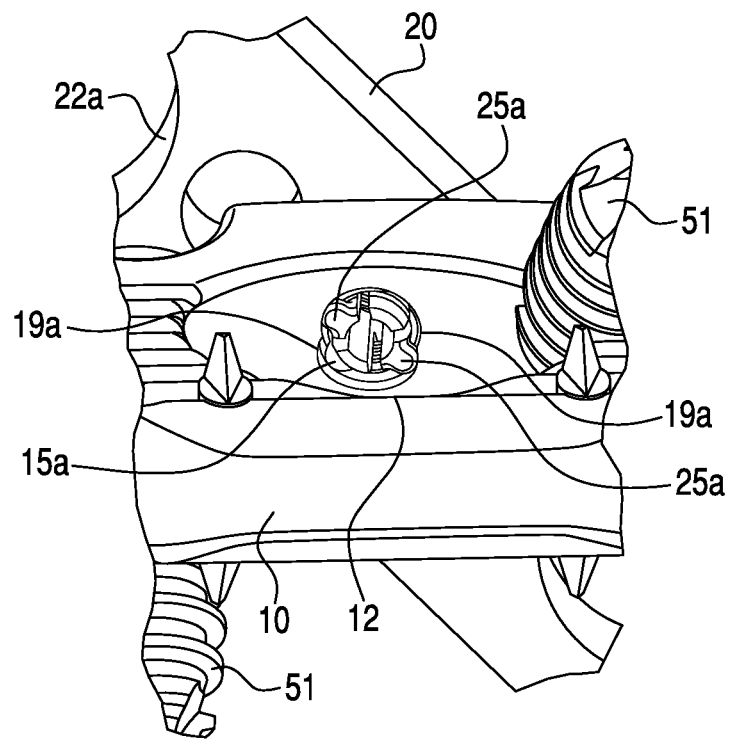
FIG. 6 is a rear posterior/inferior perspective view of the cage and plate of FIG. 5A in the final attachment position.

FIG. 6 is a close-up rear posterior/inferior perspective view of the cage 10 and plate 20 in a final locked position. Once the plate 20 has been rotated though a specific arc (in this case, approximately 90 degrees) the flange portions 25a can be configured to engage with (and be locked adjacent) the hard stop structure(s) 19a. The hard stop structure(s) 19a can be configured as an outdent or other protruding structure that extends from an interior wall into the keyway 25. For example, the hard stop structure 19a can be formed as a type of ramp such that an outermost peripheral portion of the flange portion(s) 25a slowly engages the ramp during rotation until frictional forces prevent further rotation between the flange portion(s) 25a and the hard stop(s) 19a (ramps). Alternatively, the ramp(s) can include an indent which the flange portion(s) 25a snap into upon arrival. Such structure could provide both an audible and tactile sensation to the user to indicate that the final locked position has been achieved. In order to define the amount of rotation required to arrive at the locked position, the hard stop 19a can be spaced a predetermined distance from the at least one flange opening 15a. The hard stop 19a can be configured to lock the plate 20 with respect to the cage 10 such that the user or practitioner is confident that the positional relationship between the cage 10 and plate 20 is accurate and ready for installation in between the vertebrae to provide the above-stated benefits associated with the procedure (e.g., stabilization of vertebrae, proper spacing between vertebrae, etc.)

Figure 7:
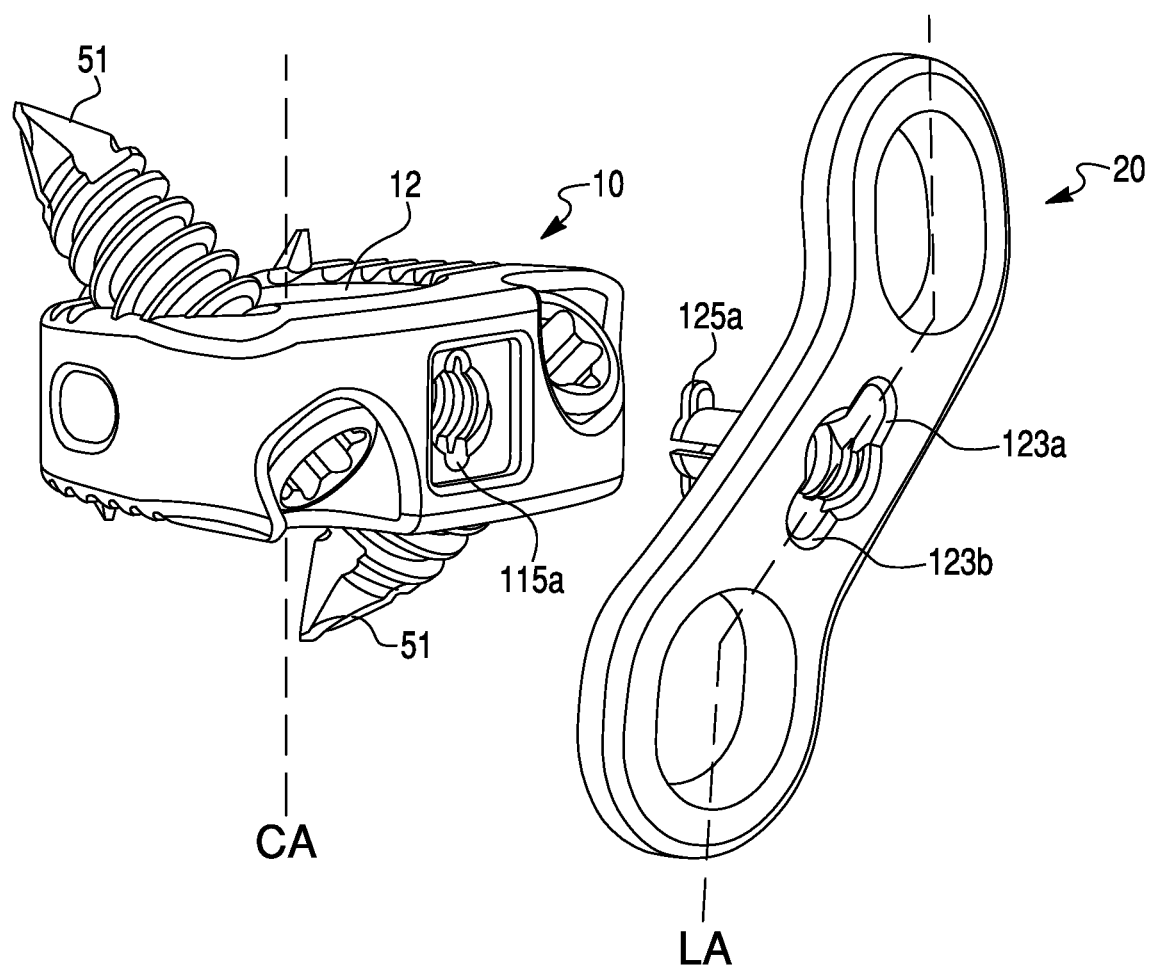
FIG. 7 is a perspective anterior view of another embodiment of a cage and plate device and system made in accordance with principles of the disclosed subject matter.

FIG. 7 is a perspective posterior view of another embodiment of a cage and plate device/system made in accordance with principles of the disclosed subject matter. In this embodiment, flange portions 125a are oriented such that they extend at an angle relative to a longitudinal axis LA of the plate 20 when viewed from a front of the plate 20. This angle is different from the angle at which flange portions 25a are oriented with respect to the plate 20 of, for example, FIG. 2A, where the flanges 25a extend at an angle of zero degrees with respect to the longitudinal axis of the plate 20. The keyway flange openings 115a, as shown in FIG. 7, can be oriented such that they extend in a direction substantially parallel with the a central axis CA of the cage aperture 12 (i.e., substantially vertically).

Installation indents 123a, 123b can be formed in a front anterior surface of the plate 20 on either side of the keyway 125 such that an installation tool can be threaded into an internal surface of keyway 125 while projections on the installation tool lock into indents 123a, 123b. Thus, relative rotation between the plate 20 and insertion tool can be prevented during installation due to the projections on the installation tool locking into indents 123a, 123b. The indents 123a, 123b can be formed in various manners, such as slots, apertures extending entirely through plate 20, projection structures that mate with the projections on the installation tool, etc.

Figure 8A:
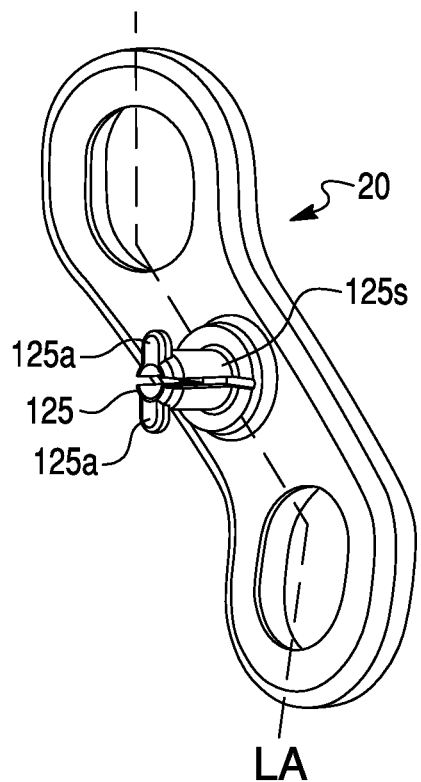
FIG. 8A is a perspective posterior view of the plate of FIG. 7.

FIG. 8A is a perspective posterior view of the plate 20 of FIG. 7 which shows the angular relationship between the extension direction of the flanges 125a and the longitudinal axis LA of plate 20. It should be noted that the plate 20 itself can also be arched such that the longitudinal axis LA curves inward towards the key 125 at the top and bottom of the plate 20 in order to facilitate mating with a bone or tissue surface. The shaft 125s of the key 125 can also be split such that the flanges 125a can move relative to each other while being biased to return to an original position under a predetermined biasing force.

Figure 8B:
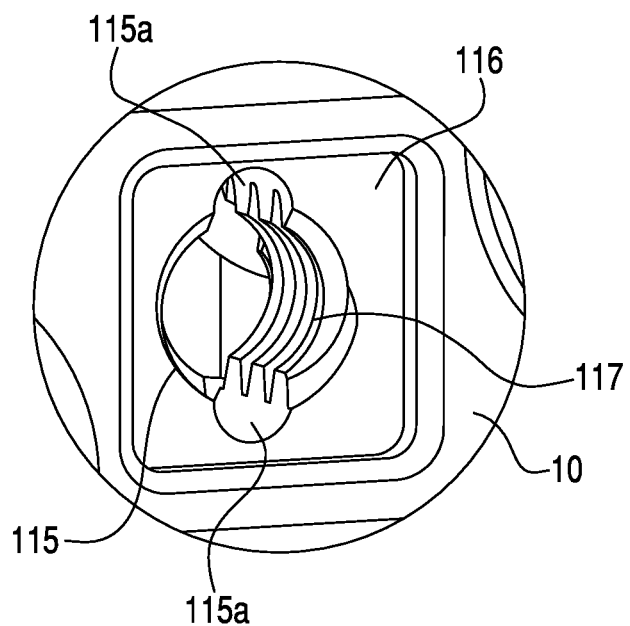
FIG. 8B is a partial perspective anterior view of the cage of FIG. 7.

FIG. 8B is a front anterior view of the cage 10 of FIG. 7 in which a keyway 115 is located within a square indent 116 in an exterior surface of the cage 10. The keyway 115 can include diametrically opposed flange openings 115a that extend in an upward and downward direction, respectively. Moreover, the flange openings 115a can extend in a direction that is substantially parallel with the central axis CA of the main aperture 12 of the cage 10. The relative positioning and structural configuration of both the keyway 115 and key 125 allow the cage 10 and plate 20 to lock together at different positional relationships as compared to the positional relationship of the cage 10 and plate 20 shown in FIG. 1. The different lock positions, as well as the different locking motions, allow for creative and efficient arrangement of the cage 10 and plate 20 system along a spinal column. Specifically, when a plurality of cage 10 and plate 20 sets are used adjacent each other to stabilize a portion of a spinal column, the spacing between cage 10 and plate 20 sets can be minimal. Thus, because the orientation and relative configuration of the plate 20 relative to the cage 10 is different in these two respective plate 20 and cage 10 sets (i.e., the set of FIG. 1 and the set of FIG. 7), in certain applications, each plate 20 will be able to be oriented in a stacked manner along a spinal column (for example as shown on FIG. 8C). Other features that can enhance efficiency of spacing between different cage 10 and plate 20 sets include different physical sizes of the plate 20 and different orientations of attachment apertures, etc.

Figure 8C:
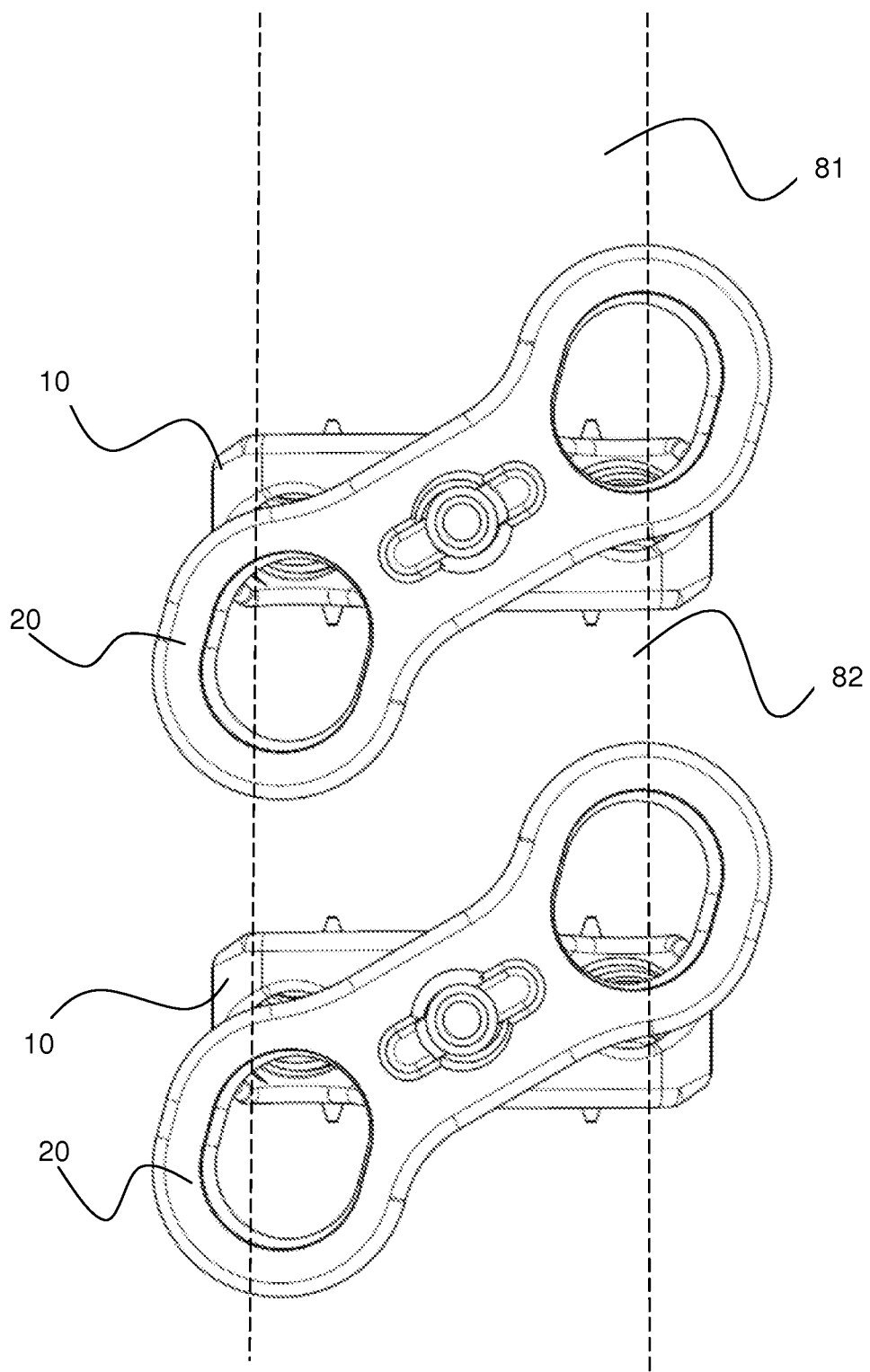
FIG. 8C is an illustration of a pair of interbody devices oriented in a stacked manner along a spinal column.

In FIG. 8C, when stacked, the adjacent cages 10 can be oriented in a similar manner with respect to the adjacent vertebrae 81, 82. However, the plates 20 can be locked at different rotational amounts with respect to each respective cage 10 such that the plates 20 do not contact each other when in a stacked configuration, and such that different structural configurations for adjacent vertebrae 81, 82 can be accounted for when locking the device or system to the spine. In FIG. 8C, one of the stacked cage and plate sets can be referred to as a secondary cage and a secondary plate. For example, the cage and plate located adjacent to the vertebrae 81 can be referred to as the secondary cage and the secondary plate.

Figure 9B:
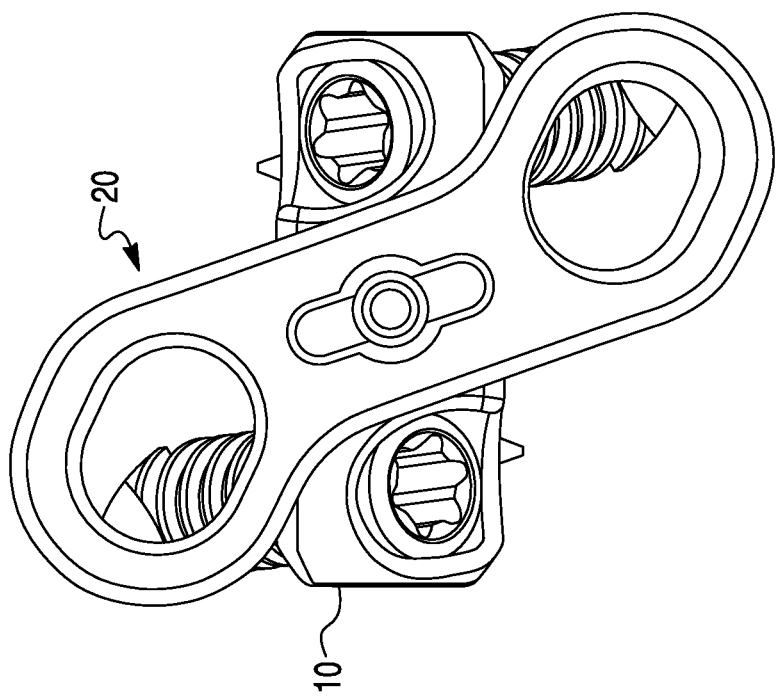
FIG. 9B is a front anterior view of the cage and plate of FIG. 7 in a counterclockwise farthest locked position.
Figure 9A:
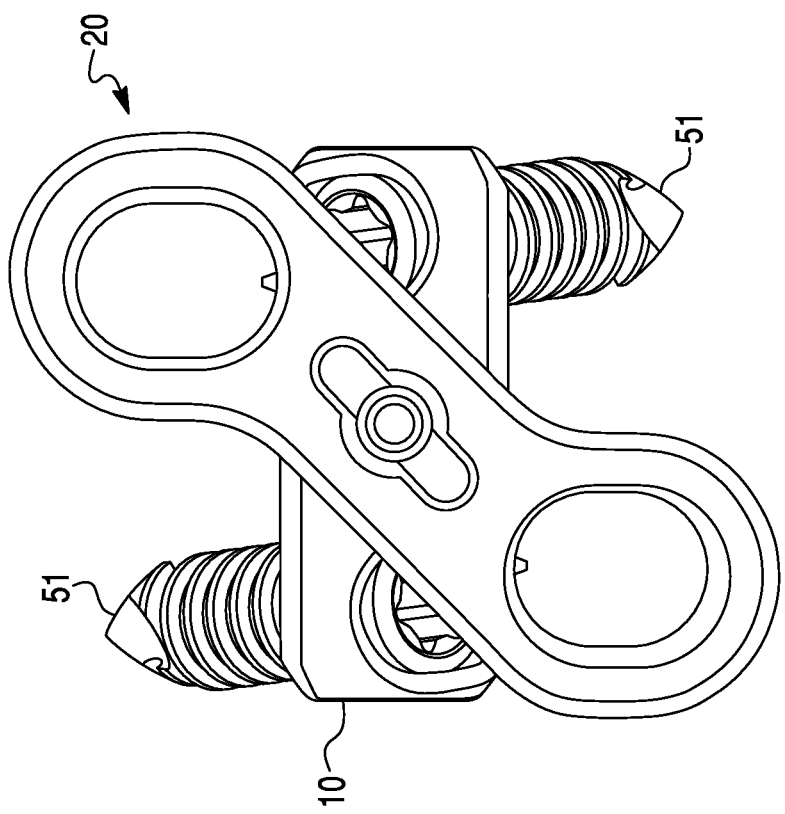
FIG. 9A is a front anterior view of the cage and plate of FIG. 7 in an initial attachment position.

FIG. 9A is a front anterior view of the cage 10 and plate 20 of FIG. 7 in an initial attachment position. As shown, the longitudinal axis of the plate 20 is at a substantially (exactly or approximately) 45 degree angle with respect to the central axis CA of the main aperture 12 of the cage 10. In this orientation, the flange portions 125a of the key 125 can extend upward and downward (vertically) from a substantially cylindrical main shaft of the key 125 such that the flange portions 125a can be inserted into the keyway 115 in the cage 10. Likewise, the flange openings 115a of the cage 10 can also extend upward and downward (vertically) in order to mate with the flange portions 125a to allow the above-described mating. In the position shown in FIG. 9A, the geometry of the keyway 115 and the key 125 can be configured such that linear movement between the cage 10 and plate 20 is permitted in a direction toward and away from each other (into and out of the plane of the drawing), while relative rotation between the cage 10 and plate 20 is prevented between the initial position and end position (i.e., relative rotation is prevented when the key 125 initially engages the keyway 115 and throughout the insertion motion until the key 125 is fully inserted into the keyway 115).

Alternatively, the key 125 could be permitted to rotate and lock with respect to the keyway 115 at specific predetermined locations along the length of the keyway 115 to allow for an adjustable or selectable locking distance between the cage 10 and plate 20. Such an embodiment could include a plurality of shelves (i.e., lock rails 13) that are accessed by openings along the length of the keyway 115. The key 125 would be rotatable at each of the openings to ride along a separate shelf which, once engaged by the flange portions 125a, could be configured to prevent linear motion between the cage 10 and plate 20 towards and/or away from each other. Each of these shelves or lock rails 13 could include a hard stop structure that would lock the cage 10 with respect to the plate 20 at a predetermined rotational position with respect to each other upon reaching that hard stop structure.

FIG. 9B is a front anterior view of the cage and plate of FIG. 7 in a counterclockwise farthest locked position. After the key 125 of cage 10 is linearly inserted to a position in the keyway 115 at which a lock rail 13 is located, the cage 10 can then be rotated to a farthest locked position at which point a hard stop can be provided to prevent further relative rotation. In the embodiment shown in FIG. 9B, the farthest locked position is located substantially 90 degrees from the initial insertion position and rotated counterclockwise as viewed from an anterior position along a central axis of the keyway 115. A lock rail 13 or shelf can be positioned such that the plate 20 can only be rotated counterclockwise with respect to the cage 10 after the key 125 reaches a predetermined position within the keyway 115. However, it is contemplated that the keyway 115 and lock rail 13 can be configured to also allow for optional clockwise rotation. In addition, a final locked position need not be the farthest locked position as defined above. For example, once the plate 20 and cage 10 are attached via key 125 and keyway 115, slight rotation of the two components (cage 10 and plate 20, relative to each other) will cause the components to become initially locked together. The user can then choose the final plate position between a range of positions between this initial locked position and the furthest locked position, depending on the particular application and other variables such as size and shape of bone and surrounding tissue, etc.

Figure 9C:
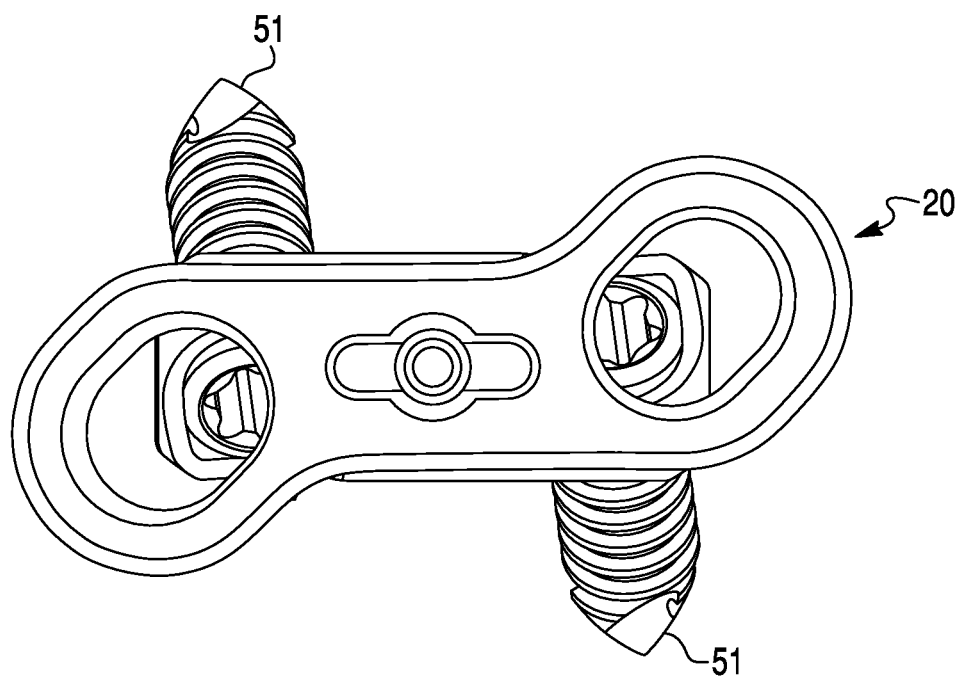
FIG. 9C is a front anterior view of the cage and plate of FIG. 7 in a clockwise farthest locked position.

FIG. 9C is a front anterior view of the cage and plate of FIG. 7 in a clockwise farthest locked position. After the key 125 of cage 10 is linearly inserted to a position in the keyway 115 at which a lock rail 13 is located, the cage 10 can then be rotated clockwise to a farthest locked position. In the embodiment shown in FIG. 9C, the farthest locked position is located substantially 90 degrees from the initial insertion position and rotated clockwise as viewed from an anterior position along a central axis of the keyway 115. A lock rail 13 or shelf can be positioned such that the plate 10 can only be rotated clockwise with respect to the cage 10 after the key 125 reaches a predetermined position within the keyway 115. However, it is contemplated that the keyway 115 and lock rail 13 can be configured to also allow for optional counterclockwise rotation. Furthermore, the lock rail 13 can be configured such that counterclockwise rotation is only permitted when the key 125 is located at one or more linear locations along the keyway 115, and clockwise rotation is only permitted when the key 125 is located at one or more different linear locations along the keyway 115.

Figure 10:
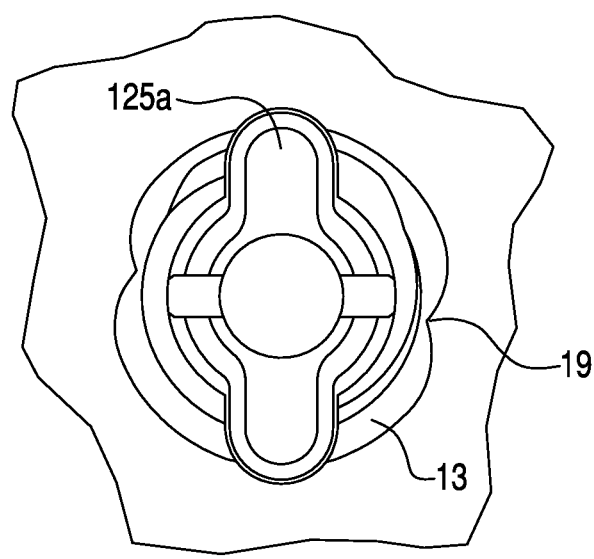
FIG. 10 is a partial posterior rear view of the cage and plate of FIG. 7 in the initial attachment position.

FIG. 10 is a partial posterior rear view of the cage and plate of FIG. 7 in the initial attachment position. The key 125 is shown fitting within keyway 115 such that the cage 10 and plate 20 can move linearly towards and away from one another (into and out of the sheet of the drawing figure). Once the key 125 is located at a fully engaged position, the flange portions 125a can then rotate over and onto the lock rail 13. Once rotation begins, the cage 10 and plate 20 can be prevented from moving linearly towards and away from one another (into and out of the sheet of the drawing figure) by interaction of the flange portions 125a on the lock rail 13 (and interaction of a surface of the plate 20 with an exterior surface of the cage 10). A hard stop structure, such as protruding ramp 19, can be provided along the lock rail 13 such that when a flange portion 125a is rotated into and contacts the hard stop structure, the protruding ramp 19 will frictionally engage with the flange portion 125a and prevent further rotational movement and/or lock the flange portion 125a (and key 125) in place with respect to the keyway 115 such that the cage 10 is locked in place with respect to the plate 20.

While certain embodiments of the invention are described above, it should be understood that the invention can be embodied and configured in many different ways without departing from the spirit and scope of the invention. For example, as explained above, the geometry of the flange portion(s) 25a and the keyway opening(s) 15a can vary considerably and remain within the contemplated scope of the present subject matter. Likewise, the keyway 15 itself and key 25 can be differently sized or shaped or oriented. The flange portions 25a could be located at an intermediate portion of a longitudinal axis of the key to allow for further structure to be placed at a distal end of the key 25.

The material from which both the plate 20 and cage 10 are made can vary considerably. For example, each of the plate 20 and cage 10 can be made from stainless steel, titanium, aluminum, alloys, ceramics, carbon fiber, PEEK, plastics, bone, and other biocompatible and/or bone regenerative materials naturally occurring or man-made materials. Each of the structures can also be supplemented with bio-compatible and/or bone/tissue regenerative materials, such as meshes or platings that can be attached or formed on surfaces of the cage 10 or plate 20. The cage 10 and plate 20 can be made from the same or different material depending on particular applications and desires of a user. The specific overall shape of the cage 10 and plate 20 can also vary widely in accordance with patient needs or user preference. The shapes can also be predetermined for a specific patient through the use of pre-operative imaging and subsequent computer modeling of each of the cage 10 and plate 20.

With respect to the various methods that can be used to practice the presently disclosed subject matter, it is contemplated that the specific steps can be executed sequentially, but can also be executed simultaneously and/or in reverse or other orders. Relative rotation between the cage 20 and plate 10 can be in either rotational direction without departing from the scope of the disclosed subject matter. In addition, the disposition of the key and keyway can be reversed (i.e., the plate 20 can include a keyway while the cage 10 includes a key). The keyway is shown as forming a slot that is disposed at a 45 degree angle with respect to the inferior and superior surfaces of the cage 10 in order to provide efficient spacing for the keyway and key. However, it is contemplated that the location of the flange openings can form a slot at different angles other than 45 degrees with respect to the inferior and superior surfaces. In addition, the flange opening may not necessarily be diametrically opposed to each other so as not to form a slot like opening for the flanges. Other insertion tools could be used with the cage 10 and plate 20, including an insertion tool that does not require threads and matching threads for attachment and insertion of the various structures. For example, the insertion tool can be formed as a clamp or can include a rivet, cam, trocar, pin, or other locking structure for attaching to the plate 20 and/or cage 10.

The number of flange portions and flange openings need not be equal. There could be more flange openings than flange portions such that a user can choose from a number of potential starting positions of relative rotation between the cage 10 and plate 20. In addition, there can be a single or multiple hard stop structures. The hard stop structures 19, 19a are shown located on and integral with the lock rail 13. However, the hard stop structures could be separate structures that are attached to the cage 10 by a suitable attaching structure or material. The hard stop structures could also be located away from the lock rail 13. In particular, the hard stop structures could be located on either anterior or posterior surfaces of the cage 10 and plate 20 that mate with each other, respectively. For example, dimple(s) could be provided on a posterior surface of the plate 20 while mating protrusions could be formed or attached to the anterior surface of the cage 10. Various other structures, such as ramps, cams, lock pins, etc., can be used as a hard stop structure to rotationally lock the cage 10 with respect to the plate 20.

The cage and plate as depicted can be used for the cervical region of the spinal column. However, it is contemplated that the disclosed subject matter could be employed in other areas of the spinal column. For example, if the cage and plate are enlarged and shaped slightly differently, the device, system and method can be used in the lumbar and/or thoracic regions of the spine. The device, system and method can be used in vivo on human beings but can also be used for teaching purposes in cadavers, and plastic or other model spinal columns. In addition, the device, system and method can be used in veterinarian practices for invertebrate animals.

It should be noted that any specific feature from any or each of the disclosed or contemplated embodiments can be used in conjunction with or swapped with like features of other embodiments. For example, the installation upper indent/aperture 23*a* and installation lower indent/aperture 23*b* can be added or removed from any of the embodiments. In addition, the specific geometrical shape for various structures, including the flanges 25*a*, 125*a*, keyways 15, 115, apertures 22*a*, etc., can be interchanged between any of the embodiments. The key 25, 125 can be solid or slotted in any of the embodiments, and can also be shaped variously in the different embodiments depending on user preference or particular application parameters.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. A spinal interbody system configured to be inserted between adjacent vertebrae of a spinal column, comprising:
   a cage;
   a plate configured to be attached to the cage;
   a keyway associated with one of the cage and the plate, the keyway having a non-uniform outer circumference located in a plane perpendicular to a central axis of the keyway; and
   a key located adjacent one of the cage and the plate, the key including a shaft and at least one flange extending from a distal end of the shaft, wherein
   the key and keyway are configured to correspond with each other and such that the plate can be moved between an unlocked position and a locked position relative to the cage, and such that the plate is prevented from rotational movement relative to the cage during a first linear movement portion along an entire extent of the keyway where the plate moves linearly towards the cage to an engaged position, and such that the plate is prevented from linear movement relative to the cage during a second rotational movement portion of the plate relative to the cage while the plate and cage are located at the engaged position, wherein
   the key is insertable into the keyway in a rotational orientation of the key with respect to the keyway and such that the key is not insertable into the keyway in another rotational orientation of the key with respect to the keyway, and wherein
   the cage includes a cage first aperture configured for use with a first cage bone screw, and a cage second aperture configured for use with a second cage bone screw.

2. The spinal interbody system of claim 1, wherein the cage is configured to be placed between adjacent vertebrae of the spinal column, the cage including an exterior surface;
   the plate includes a first surface facing the exterior surface of the cage, the plate configured to be attached to at least one of the adjacent vertebrae;
   the key is located between the exterior surface of the cage and the first surface of the plate; and
   the keyway is located in at least one of the first surface of the plate and the exterior surface of the cage and configured to receive the key therein.

3. The spinal interbody system of claim 2, wherein the shaft of the key extends from a respective one of an anterior surface of the cage and a posterior surface of the plate.

4. The spinal interbody system of claim 2, wherein the shaft of the key is a solid shaft and the at least one flange is located at a distal end of the solid shaft.

5. The spinal interbody system of claim 2, further comprising:
   two flanges each formed as substantially flat planar extensions that are substantially perpendicular to a longitudinal axis of the shaft.

6. The spinal interbody system of claim 5, wherein the two flanges are diametrically opposed to each other.

7. The spinal interbody system of claim 2, further comprising:
   two flanges each shaped differently with respect to each other.

8. The spinal interbody system of claim 2, wherein the cage includes an aperture extending therethrough and substantially perpendicular to the central axis of the keyway.

9. The spinal interbody system of claim 8, wherein the keyway extends from the exterior surface of the cage to the aperture located in the cage.

10. The spinal interbody system of claim 2, wherein the keyway is configured as a cylindrical aperture with at least one flange opening extending from a periphery of the cylindrical aperture.

11. The spinal interbody system of claim 10, wherein the keyway includes a backing surface located at and encompassing a distal end of the cylindrical aperture, the backing surface including a hard stop structure spaced a predetermined distance from the at least one flange opening and configured to abut against a portion of the key when the plate and cage are in a farthest locked position with respect to each other.

12. The spinal interbody system of claim 11, wherein the key and the keyway are configured such that the plate and cage are freely moveable towards each other when the key is located in the keyway, and such that the plate and cage are locked with respect to each other when the key and keyway are rotated a predetermined amount with respect to each other.

13. The spinal interbody system of claim 11, wherein the hard stop is configured to create an audible and tactile sensation when the key is abutted against the hard stop.

14. The spinal interbody system of claim 2, wherein
the plate is configured as an "S-shaped" structure having a center portion with a longitudinal axis extending between a top end and a bottom end of the center portion, the plate includes a top extension with top longitudinal axis extending from the top end of the center portion and at an angle away from the longitudinal axis of the center portion, the plate also includes a bottom extension with bottom longitudinal axis extending from the bottom end of the center portion and at an angle away from the longitudinal axis of the center portion.

15. The spinal interbody system of claim 14, wherein
the top extension includes an aperture configured for use with a top bone screw, and the bottom extension includes an aperture configured for use with a bottom bone screw.

16. The spinal interbody system of claim 15, wherein
the plate is configured such that a portion of the plate substantially covers at least one of the cage first aperture and the cage second aperture when the plate is in a furthest locked position with respect to the cage in order to prevent a corresponding one of the first cage screw and the second cage screw from backing out of the cage.

17. The spinal interbody system of claim 2, wherein
the cage includes a top surface and a bottom surface with an aperture extending from the top surface to the bottom surface, and at least one spike is located adjacent the aperture and extends from the top surface such that the spike is configured to prevent movement of the cage relative to the adjacent vertebrae.

18. The spinal interbody system of claim 1, wherein
the keyway is configured as a substantially cylindrical aperture extending from an exterior surface of one of the cage and plate, the aperture including at least one flange opening extending from a periphery of the aperture and extending parallel with a longitudinal axis of the cylindrical aperture, the keyway including a backing surface substantially perpendicular to the longitudinal axis of the cylindrical aperture and including a hard stop structure spaced a predetermined distance from the at least one flange opening, the hard stop configured to abut against a portion of the key when the plate and cage are in a locked position with respect to each other.

19. The spinal interbody system of claim 1, wherein
the shaft includes a slot extending in a direction parallel with a longitudinal axis of the shaft such that the shaft is divided into at least two spring portions, and the at least one flange is located at a distal end of one of the at least two spring portions such that the at least one flange is moveable towards and away from the longitudinal axis of the shaft under bias of the one of the at least two spring portions.

20. The spinal interbody system of claim 1, further comprising:
a secondary cage configured to be located adjacent the cage; and
a secondary plate configured to be moveable between a secondary unlocked position and a secondary locked position relative to the secondary cage.

21. The spinal interbody system of claim 1, further comprising:
a secondary cage including a secondary keyway extending from an exterior surface of the secondary cage to an interior surface in the secondary cage and along a secondary keyway central axis, the secondary cage defined by a secondary cage upper surface and a secondary cage lower surface with a secondary cage opening extending between the secondary cage upper surface and secondary cage lower surface, the secondary cage opening having a secondary cage opening central axis that extends substantially perpendicular to the secondary keyway central axis; and
a secondary plate including a secondary key configured to be attached via the secondary keyway to the secondary cage such the secondary plate can be moved between a secondary unlocked position and a secondary locked position relative to the secondary cage, wherein
when the secondary plate is located at the secondary locked position relative to the secondary cage, a secondary longitudinal axis of the secondary plate is oriented at a first angle with respect to the secondary cage opening central axis,
the cage is defined by an upper surface and a lower surface with an opening extending between the upper surface and lower surface, the opening having an opening central axis that extends substantially perpendicular to the keyway central axis, and
when the plate is located at the locked position relative to the cage, a longitudinal axis of the plate is oriented at a second angle with respect to the opening central axis, and
the first angle is different from the second angle such that the cage and plate are configured to be used adjacent the secondary cage and secondary plate in a spinal column.

22. A method for manufacturing the spinal interbody system of claim 1, comprising:
fabricating the cage such that the cage is configured to be placed between adjacent vertebrae of a spinal column, the cage including an exterior surface;
fabricating the plate such that the plate includes a first surface facing the exterior surface of the cage, and such that the plate is configured to be attached to at least one of the adjacent vertebrae;
fabricating the key located between the exterior surface of the cage and the first surface of the plate; and
fabricating the keyway such that the keyway is located in at least one of the first surface of the plate and the exterior surface of the cage and is configured to receive the key therein, wherein
the key includes a shaft and at least one flange extending from the shaft such that the key is insertable into the keyway in a specific rotational orientation of the key with respect to the keyway and such that the key is not insertable into the keyway in another specific rotational orientation of the key with respect to the keyway.

23. A spinal interbody system configured to be inserted between adjacent vertebrae of a spinal column, comprising:
a cage;
a plate configured to be attached to the cage;
a keyway associated with one of the cage and the plate, the keyway having a non-uniform outer circumference located in a plane perpendicular to a central axis of the keyway; and
a key located adjacent one of the cage and the plate, the key including a shaft and at least one flange extending from a distal end of the shaft, wherein
the key and keyway are configured to correspond with each other and such that the plate can be moved between an unlocked position and a locked position relative to the cage, and such that the plate is prevented from rotational movement relative to the cage during a first linear movement portion along an entire extent of the keyway where the plate moves linearly towards the cage to an engaged position, and such that the plate is prevented from linear movement relative to the cage during a second rotational movement portion of the plate relative to the cage while the plate and cage are located at the engaged position, wherein the shaft includes a slot extending in a direction parallel with a longitudinal axis of the shaft such that the shaft is divided into at least two portions, and the at least one flange is located at a distal end of one of the at least two portions such that the at least one flange is moveable towards and away from the longitudinal axis of the shaft, wherein the key is insertable into the keyway in a rotational orientation of the key with respect to the keyway and such that the key is not insertable into the keyway in another rotational orientation of the key with respect to the keyway, and wherein the cage includes a cage first aperture configured for use with a first cage bone screw, and a cage second aperture configured for use with a second cage bone screw.

\* \* \* \* \*